: US009631618B2

United States Patent
Shoykhet et al.

(10) Patent No.: US 9,631,618 B2
(45) Date of Patent: Apr. 25, 2017

(54) DETERMINATION OF A FLUID LOSS OF A PISTON PUMP BASED ON EVACUATION TIME VARIATION

(71) Applicant: AGILENT TECHNOLOGIES, INC., Loveland, CO (US)

(72) Inventors: Konstantin Shoykhet, Karlsruhe (DE); Klaus Witt, Keltern (DE)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/677,558

(22) Filed: Apr. 2, 2015

(65) Prior Publication Data

US 2015/0285239 A1    Oct. 8, 2015

(30) Foreign Application Priority Data

Apr. 2, 2014    (DE) .................. 10 2014 104 708

(51) Int. Cl.

| | | |
|---|---|---|
| *F04B 51/00* | (2006.01) | |
| *F04B 23/06* | (2006.01) | |
| *F04B 49/08* | (2006.01) | |
| *F04B 49/20* | (2006.01) | |
| *G01N 30/32* | (2006.01) | |
| *G01N 30/36* | (2006.01) | |

(52) U.S. Cl.
CPC .............. *F04B 51/00* (2013.01); *F04B 23/06* (2013.01); *F04B 49/08* (2013.01); *F04B 49/20* (2013.01); *G01N 30/32* (2013.01); *G01N 30/36* (2013.01); *G01N 2030/326* (2013.01)

(58) Field of Classification Search
CPC .. F04B 49/00; F04B 51/00; F04B 2201/0202; F04B 2201/0203; F04B 2201/0207; F04B 2201/0208; F04B 2201/0803; F04B 2205/09; G01N 2030/326; G01N 30/6021; G01N 30/6026
USPC ....................................... 73/47, 49.7
See application file for complete search history.

(56) References Cited

U.S. PATENT DOCUMENTS

| | | | | |
|---|---|---|---|---|
| 4,714,545 A | * | 12/1987 | Bente ..................... | F04B 13/02 210/101 |
| 6,807,851 B2 | * | 10/2004 | Wakahara .......... | F02M 25/0809 73/114.38 |
| 2005/0061722 A1 | * | 3/2005 | Takao ..................... | F04B 9/02 210/137 |

(Continued)

FOREIGN PATENT DOCUMENTS

| | | |
|---|---|---|
| EP | 0309596 B1 | 4/1989 |
| EP | 1918705 A1 | 5/2008 |

(Continued)

*Primary Examiner* — Bryan Lettman
*Assistant Examiner* — Timothy Solak

(57) ABSTRACT

A device for determining a leakage of fluid in a piston pump, wherein the piston pump comprises a piston arranged in such a manner that it can reciprocate in a piston chamber for delivering fluid, wherein the device comprises a control unit for controlling the piston in such a manner that the piston executes two piston chamber evacuation processes with different evacuation times, in each case for at least partial evacuating of fluid located in the piston chamber, and a determination unit for determining the leakage based on a comparison of fluid quantities evacuated from the piston chamber in the two piston chamber evacuation processes.

13 Claims, 3 Drawing Sheets

(56) References Cited

U.S. PATENT DOCUMENTS

| | | | | |
|---|---|---|---|---|
| 2005/0147508 A1* | 7/2005 | Luongo | ............... | F04B 51/00 |
| | | | | 417/415 |
| 2006/0288803 A1* | 12/2006 | Weissgerber | .......... | G01N 30/36 |
| | | | | 73/865.8 |
| 2007/0084766 A1* | 4/2007 | Ishii | ................ | G01N 30/32 |
| | | | | 210/87 |
| 2008/0092639 A1* | 4/2008 | Lee | ................ | G01N 30/32 |
| | | | | 73/61.52 |
| 2010/0275678 A1* | 11/2010 | Herzog | ............. | F04B 11/0058 |
| | | | | 73/61.56 |

FOREIGN PATENT DOCUMENTS

EP         2244091         10/2010
WO     WO2005050190 A2     6/2005

* cited by examiner

DETERMINATION OF A FLUID LOSS OF A PISTON PUMP BASED ON EVACUATION TIME VARIATION

PRIORITY CLAIM

The present application claims priority under 35 U.S.C. §119(e) from German Patent Application No. 102014104708.7 filed on Apr. 2, 2014 naming Konstantin Shoykhet, et al. as inventors. The entire disclosure of German Patent Application No. 102014104708.7 is specifically incorporated herein by reference.

TECHNOLOGICAL BACKGROUND

The present invention relates to a device and a method for determining a leakage of fluid in a piston pump, an arrangement, and a sample separation instrument.

In high performance liquid chromatography (HPLC) a liquid (mobile phase) is typically moved at a very accurately controlled flow rate (for example, in the range from microliters to milliliters per minute) and at a very high pressure (typically 20 to 1000 bar and higher, currently up to 2000 bar), in which the compressibility of the fluid can be noticeable, through a so-called stationary phase (for example, in a chromatographic column), in order to separate individual components of a sample liquid introduced into the mobile phase from one another. Such an HPLC system is of known art, for example from EP 0,309,596 B1 of the same applicant, Agilent Technologies, Inc.

The pump, which delivers the mobile phase at the high pressure, can have a piston reciprocating in a piston chamber, which undertakes the displacement of the fluid. During the operation of a pump it can be important for the correct control of the latter to obtain information concerning possible leaks in the pump.

EP 2,244,091 of the same applicant, Agilent. Technologies, Inc., discloses as sample separation device for separating a sample, wherein the sample separation device comprises a first fluid line for conducting a first fluid, a second fluid line for conducting a second fluid, and a sample separation instrument for separating the sample. A mixing point is fluidically or in a fluidic manner connected with the first fluid line and the second fluid line and is arranged downstream of these. The mixing point serves to mix the first fluid with the second fluid and delivers a mixed fluid composition to the sample separation unit for separating the sample. A leak detection unit is provided for detecting any leakage upstream of, or at the mixing point.

DISCLOSURE

It is an object of the invention to determine any possible leakage from a piston pump precisely and in a reliable manner.

In accordance with an exemplary example of embodiment of the present invention a method is provided in such a manner that in a piston pump two or more piston chamber evacuation processes are executed, in each case for at least partial evacuating of fluid located in the piston chamber, with different evacuation times (that is to say, time periods of different lengths, over which the respective partial or complete evacuation of the piston pump takes place), and a determining of the leakage takes place based on a comparison of fluid quantities evacuated from the piston chamber in at least two piston chamber evacuation processes of different lengths.

In accordance with an exemplary example of embodiment of the present invention a device is created for purposes of determining a leakage of fluid (that is to say a liquid and/or a gas, optionally comprising solid body particles) in a piston pump, wherein the piston pump comprises a piston arranged such that it can reciprocate (that is to say, it can move backwards and forwards in a piston chamber for purposes of delivering fluid, wherein the device comprises a control unit for purposes of controlling the piston in such a manner that the piston executes two or more piston chamber evacuation processes, in each case for at least partially evacuating fluid located in the piston chamber, with different evacuation times (that is to say, time periods of different lengths over which the respective partial or complete evacuation of the piston pump takes place), and comprises a determination unit for purposes of determining the leakage based on a comparison of fluid quantities evacuated from the piston chamber (in particular, fluid volumes or fluid masses evacuated) in the two piston chamber evacuation processes.

In accordance with another exemplary example of embodiment of the invention an arrangement is provided, which comprises a piston pump for purposes of delivering fluid, which comprises a piston arranged such that it can reciprocate in the piston chamber, and a device with the above-described features for purposes of determining a leakage of fluid in the piston pump.

In accordance with another exemplary example of embodiment of the present invention a sample separation instrument is provided for purposes of separating a fluidic sample present in a mobile phase into fractions, wherein the sample separation instrument comprises (a) a piston pump, which comprises a piston arranged such that it can reciprocate in a piston chamber for purposes of delivering fluid as a mobile phase, and is designed for purposes of driving the mobile phase through the sample separation instrument, (b) a separation unit downstream of the piston pump for separating the different fractions of the sample present in the mobile phase, and (c) a device with the above-described features for determining a leakage of fluid in the piston pump.

In accordance with yet another exemplary example of embodiment a method is provided liar purposes of determining a leakage of fluid in a piston pump, wherein the piston pump comprises a piston arranged in such a manner that it can reciprocate in a piston chamber for purposes of delivering fluid, wherein in the method the piston is controlled such that the piston executes two piston chamber evacuation processes, in each case for purposes of at least partial evacuation of the fluid located in the piston chamber, with different evacuation times, and the leakage is determined based on a comparison of fluid quantities evacuated from the piston chamber in the two piston chamber evacuation processes.

In accordance with an exemplary example of embodiment a leakage of a piston pump can be determined in that the piston in the piston chamber is activated at least twice, in each case with different speeds, for purposes of delivering flu id from the piston chamber into a connected system. In the case of a longer duration of the delivery process more fluid is lost, caused by the leakage, through the leak or leaks than in the case of a shorter duration of the delivery process, since the leak can then act over a longer time period so as to reduce the fluid volume. A fluid balance, which compares the two piston chamber evacuation processes of different durations with one another, then allows the determining of a higher fluid quantity discrepancy in the case of the slower execution of the piston chamber evacuation process, as compared with the faster execution of another piston chamber evacuation process. By this means a qualitative or quantitative determination is made possible for the scale of a leak, or fluid loss, from the piston pump, in particular from its piston chamber, more in particular through its piston seals.

In what follows additional configurations of the device, the arrangement, the sample separation instrument, and the method are described.

In accordance with an example of embodiment the control unit can be set up for purposes of controlling the piston such that the two piston chamber evacuation processes are carried out with (associated with the different evacuation times) different evacuation velocities (in particular different piston evacuation velocities relative to the piston chamber during the evacuation), different flow rates (that is to say, fluid volumes evacuated per unit of time), and/or different delivered volumes (that is to say, total fluid volumes evacuated). In accordance with one configuration the evacuation times for the two piston chamber evacuation processes can be selected to be of different length, that is to say, the time period over which the piston is moved in the piston chamber for purposes of removing fluid from the piston chamber. It is also possible to adjust the evacuation flow rates, that is to say, the fluid volume delivered per unit of time, such that they are different fir the two piston chamber evacuation processes. Also the evacuation of fluid volumes of different sites at different piston movement velocities is suitable for qualifying the leakage, or even for quantifying the leakage.

In accordance with an example of embodiment the determination unit can be set up so as to determine the leakage based on a difference between the fluid quantity evacuated in the piston chamber evacuation process with the longer evacuation time, and the fluid quantity evacuated in the piston chamber evacuation process with the shorter evacuation time. In this case, the fluid quantity can be a fluid volume or a fluid mass. Since in the case of the longer evacuation tune fluid in the piston pump can escape from the system over a longer time period, the fluid balance for the longer evacuation time results in a higher loss than in the case of the shorter evacuation time. In this case, it is to be taken into account that, by virtue of the longer duration of the evacuation time, the volume passed to the system can now also turn out to be higher. This effect can advantageously be taken into account. This can occur by means of an estimation of the volume passed to the system over the measurement time i.e. the evacuation time, but preferably by means of as comparison of the balances over two equally long measurement intervals (whereby the volumes passed to the system can be compared with one another), which in each case include an evacuation process, wherein the evacuation times of these evacuation processes are different.

In accordance with an example of embodiment the control unit can be set up, based on the determined leakage, to adapt the piston movement so as to compensate at least partially for the missing fluid quantity associated with the leakage (in particular, to deliver missing fluid subsequently by means of a temporary increase of the flow rate). In order to provide a precise fluid quantity or a precise flow rate (in particular a precisely adjusted solvent quantity, or solvent composition) to a fluidic system downstream of the piston pump, its piston trajectory and thus its piston movement in the piston chamber can be adapted accordingly by determining, i.e. establishing, a leakage on the piston pump so as to deliver subsequently the fluid that has been lost as a result of the leakage. This can advantageously occur during the actual operation of the piston pump for purposes of delivering a defined fluid profile, in order to compensate for missing volumes on-line respectively virtually in real-time.

In accordance with an example of embodiment the control unit can be set up for purposes of controlling the piston such that in each of the two piston chamber evacuation processes the piston can be moved out from a particular predefined initial position of the piston in the piston chanter, which is the same for the two piston chamber evacuation processes. Alternatively or additionally the control unit can be set up for purposes of controlling the piston such that the piston in each of the two piston chamber evacuation processes can be moved to a particular predefined end position of the piston in the piston chamber, which is the same for the two piston chamber evacuation processes. In that the initial position and/or the end position of the piston in the piston chamber is/are identically prescribed for the two piston chamber evacuation processes, the leakage determination evacuation processes can be executed under defined and therefore well reproducible conditions, corresponding to one another precisely; this enables a high standard of comparability and therefore a suppression of spurious accompanying factors such as, for example, leakages that are dependent on the piston location).

In accordance with an example of embodiment the control unit can be set up for purposes of controlling the piston such that for each of the two piston chamber evacuation processes the piston stroke between the particular predefined initial position and the particular predefined end position is essentially the same. In this manner completely identical trajectories can be traversed by the piston with different velocities in two comparatively executed piston chamber evacuation processes', this can deliver in particular good comparable results, in particular in the case of leakages that are dependent on the piston position.

In accordance with an example of embodiment the determination unit can furthermore be set up for purposes of determining the leakage based on at least one of a group consisting of a previously known movement profile of the piston, a recorded flow rate, and a recorded pressure. If the piston position is known at each point in time, or can be determined, the total flow rate delivered that is to say, the sum of a fluid flow rate, which is delivered into a system in a fluidic manner connected downstream of the piston pump, and another fluid flow rate that is associated with the leakage on the piston pump) can be determined from this piston position. The volume displaced by the piston in the piston chamber then corresponds to this summated fluid volume. Also with at least one flow measuring instrument and/or at least one pressure measuring instrument upstream of the piston pump the total flow, i.e. a total volume, can be determined. With at least one flow measuring instrument and/or at least one pressure measuring instrument downstream of the piston pump the system flow (that is to say, the total flow after deduction of the leakage losses), i.e. a system fluid volume (that is to say, the total volume after deduction of the leakage losses), can be determined.

In accordance with an example of embodiment the control unit can be set up to specify the two piston chamber evacuation processes such that thermal conditions in the piston pump during the two piston chamber evacuation processes are matched to one another, in particular are the same. For this purpose it can be advantageous not to initiate too fast a piston movement for the different piston chamber evacuation processes. Thus one piston chamber evacuation process could at least be selected such that decay functions of the rise in temperature caused by compression have almost petered out asymptotically, as a result of which their influence becomes negligible. Such a time constant is conditioned by the design, and can be of the order of a few seconds, for example, between one second and ten seconds.

In accordance with an example of embodiment the two piston chamber evacuation processes can each correspond to a complete span of time between the piston being located at an upper end point in the piston chamber, and the piston being located at a lower end point in the piston chamber. In other words, in each case a complete piston stroke can be traversed, in order to execute the measurements for purposes of determining the leakage. One then obtains high absolute values for the different delivered volumes in the two piston chamber evacuation processes, since the leakage can then act over the whole piston stroke in each case.

In accordance with an example of embodiment the control unit can be set up for purposes of controlling the piston such that the piston executes each one of the two piston chamber evacuation processes a plurality of times, wherein the determination unit is set up so as to determine the leakage based on averaging over the piston chamber evacuation processes that are in each case executed a plurality of times. The plurality of first piston chamber evacuation processes can either be executed directly one after another, or can be interrupted by second piston chamber evacuation processes. In a corresponding manner, the plurality of second piston chamber evacuation processes can either be executed directly one after another, or can be interrupted by first piston chamber evacuation processes. By virtue of averaging, over a plurality of piston chamber evacuation processes, artefacts in individual measurements can be suppressed, and thus the accuracy of the leakage determination can be improved.

In accordance with an example of embodiment the arrangement can have a fluidic component with a defined fluid load characteristic downstream of the piston pump (for example, one that is fixed, previously known, or self-adjusting in a reproducible manner during the operation), wherein the fluidic component is arranged so as to accommodate at least temporarily fluid evacuated during the piston chamber evacuation processes (for example, to serve as a buffer volume, or to allow the fluid to pass through it with a delay). In accordance with this configuration the fluid is evacuated during the piston chamber evacuation processes to a particular reference in the form of the fluidic component; this ensures defined conditions downstream of the piston pump. The defined fluid load, characteristic can identify the behavior of the fluidic component so as to deal with a supplied fluid load, in particular to set a defined fluidic resistance against the supplied fluid load. By this means defined fluidic conditions can be provided downstream of the piston pump for each one of the plurality of piston chamber evacuation processes.

In accordance with an example of embodiment the fluidic component can be an additional piston pump, which comprises an additional piston chamber and an additional piston arranged in such a manner that it can reciprocate in the additional piston chamber. The movements of the piston of the piston pump, or of the additional piston of the additional piston pump, can be coordinated. i.e. synchronized, with one another, such that the operating characteristics of the two piston pumps can be coordinated with each other.

For example, the two piston pumps can be operated in an operating state in which they are in a fluidic manner separated from one another, in which the piston chamber of the piston pump is filled with fluid, and the additional piston chamber of the additional piston pump independently of the former is in a fluidic manner evacuated with respect to a connected fluidic system. In contrast, in an operating state of the two piston pumps in which they are in a fluidic manner connected with one another, fluid from the piston chamber of the piston pump can be pumped by means of the piston into the additional piston chamber of the additional piston pump, and simultaneously into the fluidic system. A switch between the two operating states can be instigated by actuating a fluidic valve or the like.

If the piston of the piston pump delivers fluid in the operating state in which the piston pumps are in a fluidic manner coupled with one another, the additional piston travelling backwards in the additional piston chamber can then offer a defined fluidic resistance to the filling of the additional piston chamber, as a result of which a precisely adjusted load characteristic of the additional piston pump is defined.

In accordance with an example of embodiment the control unit can be set up for purposes of controlling the additional piston such that during the two piston chamber evacuation processes the additional piston is moved in a controlled manner such that the fluid evacuated from the piston chamber is delivered into the additional piston chamber. In other words, the above operating state, in which the piston pumps are in a fluidic manner coupled with one another, can correspond to the piston chamber evacuation process.

In accordance with an example of embodiment the control unit can be set up for purposes of controlling, i.e. regulating, the additional piston such that during the two piston chamber evacuation processes a pressure and/or a flow rate of fluid downstream of the additional piston pump is constant. Downstream of the additional piston pump a connected fluidic system (for example, a sample separation path of a sample separation instrument with a sample separation unit, for example a chromatographic separation column) can thus be continuously supplied with a defined quantity of fluid, while the assessment of the leakage properties, i.e. the leak rate, of the piston pump is executed.

In accordance with an example of embodiment the two piston chamber evacuation processes can be piston chamber transfer processes, in which fluid from the piston chamber in each case is transferred into the additional piston chamber. If, for purposes of determining the leakage, an evacuation of the piston chamber of the piston pump takes place, this can automatically lead to an at least partial filling of the additional piston chamber of the additional piston pump downstream of the piston pump. The filling of the additional piston pump is then fed by the piston chamber, so that this becomes a piston chamber transfer process.

In accordance with an example of embodiment the arrangement can have a fluidic valve located between the piston pump and the additional piston pump, whereby the control unit is set up for purposes of controlling the fluidic valve such that during the two piston chamber evacuation processes the fluidic valve allows a fluid flow through the fluidic valve, and between the two piston chamber evacuation processes prevents a fluid flow through the fluidic valve, at least temporarily. In order to configure a scenario corresponding to the above-described operating state in which the piston pumps are in a fluidic manner separated from one another, the fluidic valve can be switched such that a fluid flow from the piston pump to the additional piston pump is interrupted, i.e. is made impossible. On the other hand, in order to configure a scenario corresponding to the above-described operating state in which the piston pumps are in a fluidic manner coupled with one another, the fluidic valve can be switched such that a fluid flow from the piston pump to the additional piston pump is permitted.

In accordance with an exemplary example of embodiment the determination unit can be set up so as to determine the leakage based on a comparison, in particular a difference, between a summated fluid delivery rate (that is to say, a sum of two flow rates) of the piston and the additional piston, if the piston and the additional piston are in a fluidic manner coupled, and an individual fluid delivery rate of just the additional piston, if the piston and the additional piston are in a fluidic manner decoupled. The concept of determination of a leakage of a piston chamber by means of a comparison between at least two piston chamber evacuation processes of differing duration can, in the case of the presence of a piston pump and an additional piston pump arranged downstream of the former, be further refined in that a fluid quantity is delivered to a fluidic system connected downstream of the additional piston pump for the above operating state in which the piston pumps are in a fluidic manner separated from one another, and for the operating state in which they are in a fluidic manner coupled with one another. In the operating state in which the piston pump is in a fluidic manner decoupled from the additional piston pump, only the additional piston pump with its possible leakage contributes to a shortfall of fluid delivered into the system. In the other operating state, in which the piston pump is in a fluidic manner coupled with the additional piston pump, both the piston pump and also the additional piston pump with their possible leakages contribute to a shortfall of fluid delivered into the system. A difference between these two shortfalls in volume then corresponds to the leakage of the piston pump that is located upstream. The result from this assessment can then be compared with the result that would be obtained from the two piston chamber evacuation processes with different evacuation durations. By combining these two complementary methods of determining the leak rate of the piston pump, the accuracy of the leakage detection can be increased.

In accordance with an example of embodiment the control unit can be set up for purposes of controlling the piston and the additional piston such that between the two piston chamber evacuation processes the piston chamber is filled at least temporarily with fluid from a reservoir, and the additional piston is controlled so as to deliver fluid from the additional piston chamber into a fluidic path downstream of the additional piston pump. Thus the result can be a first process, in which the piston chamber is filled and independently from this the additional piston chamber is evacuated to the fluidic system, alternating with a second process in which both the additional piston chamber and also the fluidic system are fed from the evacuating piston chamber.

In accordance with an alternative example of embodiment the fluidic component can be a fluidic restrictor. Such a fluidic restrictor can, for example, be a specific narrowing of a fluid line, with which a predefined hydraulic resistance is generated for the fluid flowing out of the piston chamber. Also by this means a type of reference, in the sense of a component for purposes of providing defined fluid load conditions, can be provided downstream of the piston pump.

In accordance with one example of embodiment the device can be designed so as to execute the determination of the leakage while simultaneously, i.e. at the same time, executing a separation of the fluidic sample into fractions. Accordingly, with the method the determining of the leakage can be executed while a fluidic sample present in a mobile phase is being separated into fractions, whereby the fluid is delivered in the mobile phase by the piston pump. In other words, an on-line detection of the leakage of the piston pump is possible without the need for interrupting an analytical separation method for purposes of separating a fluidic sample into its fractions. A delivered fluid flow then serves both for leakage detection and also for sample separation.

In accordance with an example of embodiment the fluid pump can be a high-pressure pump for purposes of pumping a mobile phase to a separation unit of the sample separation instrument for purposes of separating different fractions of a fluidic sample present in the mobile phase. Such a high-pressure pump delivers a mobile phase in particular a solvent composition) from one or a plurality of liquid containers to a sample separation unit, such as, for example, a chromatographic separation column. In an injector device the delivered mobile phase is then mixed with the fluidic sample. Since such a high-pressure pump can be subjected to high and extremely high pressures of 1200 bar and more, the detection of and, if necessary, compensation fir, leakage is in particular important.

In accordance with an example of embodiment the sample separation unit can be designed as a chromatographic separation unit, in particular as a chromatography separation column. In a chromatographic separation process the chromatography separation column can be provided with an absorption medium. The fluidic sample can be detained on the latter, and only subsequently is more slowly, or in the presence of a specific solvent composition, again replaced by fractions, whereby the separation of the sample into its fractions is achieved.

The sample separation instrument can be a microfluidic measuring instrument, a life science instrument, a fluid chromatography instrument, an HPLC (high performance liquid chromatography) plant, a UHPLC, plant, an SEC (supercritical fluid chromatography) instrument, a gas chromatography instrument, an electrophoresis instrument, and/ or a gel electrophoresis instrument. However, man other applications are possible.

The pumping system can, for example, be set up so as to convey the mobile phase at, for example, several 100 bar, up to 1000 bar and more, through the system.

The sample separation instrument can have a sample injector for purposes of introducing the sample into the fluidic separation path. Such a sample injector can have an injection needle that can be coupled with a seating in an appropriate liquid path, whereby the needle can be traversed out of its seating, in order to accommodate a sample, whereby after the reintroduction of the needle into the seating the sample is located in a fluid path, which, for example by the switching of a valve, can be switched into the separation path of the system, which leads to the introduction of the sample into the fluidic separation path.

The sample separation instrument may comprise a fraction collector for purposes of collecting together the separated components. Such a fraction collector can, for example, guide the various components into various fluid containers. The analyzed sample can, however, also be supplied to a drain tank.

The sample separation instrument can preferably have a detector for purposes of detecting the separated components. Such a detector can generate a signal, which can be observed and/or recorded, and which is indicative of the presence and quantity of the sample components in the fluid flowing through the system.

BRIEF DESCRIPTION OF THE FIGURES

Other objectives and many of the advantages accompanying examples of embodiment of the present invention can be easily perceived and better understood with reference to the following more detailed description of examples of embodiment in conjunction with the accompanying figures. Features that are essentially or functionally the same, or similar, are provided with the same reference symbols.

Figure 1:
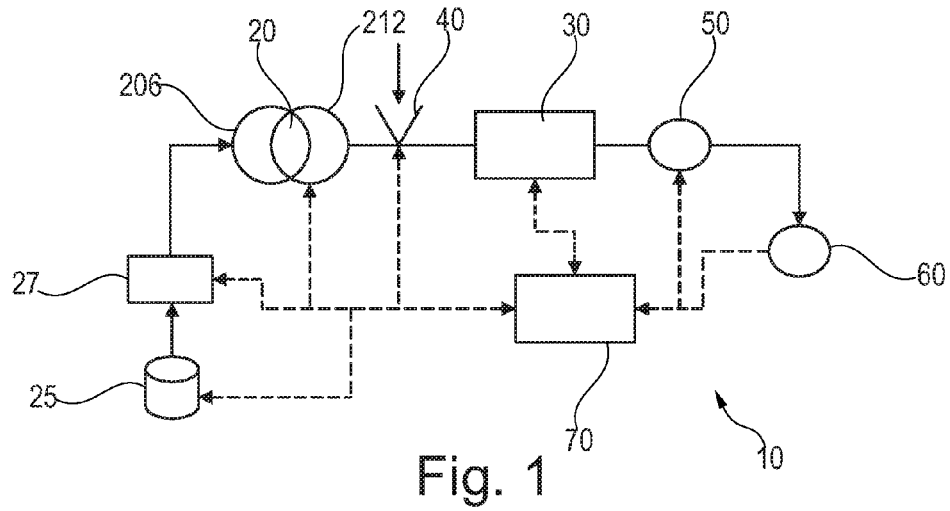
FIG. 1 shows an HPLC system in accordance with an exemplary example of embodiment of the invention.

The representations in the drawing are schematic.

FIG. 1 shows the schematic structure of an HPLC system 10, as it can be used for example, for liquid chromatography. A fluid pumping system 20, which is supplied with solvents from a supply unit 25, drives a mobile phase through a sample separation unit 30 (such as, for example, a chromatographic column), which includes a stationary phase. A degasser 27 can degas the solvents, before the latter are supplied to the fluid pumping system 20. A sample feed unit 40, here optional, is arranged between the fluid pumping system 20 and the sample separation unit 30, in order to introduce a sample liquid into the fluidic separation path. The stationary phase of the sample separation unit 30 is provided for the purpose of separating components of the sample. A detector, see flow cell 50, detects separated components of the sample, and a fractionation unit can be provided for the purpose of dispensing separated components of the sample into containers provided for this purpose. After passing the detector the liquids can be dispensed into a drain tank or a fractionation unit 60.

While a liquid path between the fluid pumping system 20 and the sample separation unit 30 is typically under high pressure, the sample liquid is introduced under normal pressure into a region separated from the liquid path, a so-called sample loop, of the sample feed unit 40, which then in turn introduces the sample liquid into the liquid path that is under high pressure. During the switching of the sample liquid in the sample loop, initially under normal pressure, into the liquid path under high pressure, the content of the sample loop is brought up to the system pressure of the sample separation instrument 10 designed as an HPLC. A control unit 70 controls the individual components 20, 25, 27, 30, 40, 50, 60 of the sample separation instrument 10.

As is schematically represented in FIG. 1, the fluid pumping system 20 can be formed from a piston pump 206 and an additional piston pump 212 arranged downstream of the former.

Figure 2:
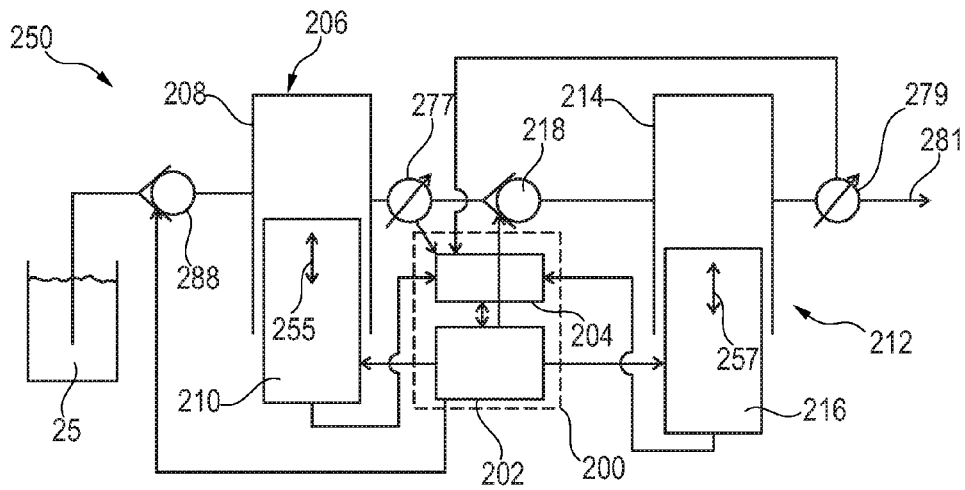
FIG. 2 shows an arrangement of two piston pumps and a device for determining a leakage of fluid in one of the two piston pumps, in accordance with an exemplary example of embodiment of the invention.

FIG. 2 shows an arrangement 250 of the two piston pumps 206, 212 and a device 200 (designed for example as a processor) for determining a leakage of fluid in one 206 of the two piston pumps arranged upstream, in accordance with an exemplary example of embodiment of the invention.

The arrangement 250 contains the piston pump 206 for purposes of delivering fluid, which comprises a piston chamber 208 and a piston 210 arranged such that it can reciprocate (see double arrow 255) in the piston chamber 208. The supply unit 25, which can for example, be designed in the form of one or a plurality of supply bottles, here provides the fluid that is to be pumped. Between the supply unit 25 and the piston pump 206 a fluidic valve 288 is arranged, with which the fluid supply from the supply unit 25 to the piston pump 206 can be selectively enabled or interrupted. The movement of the piston 210 and the switching state of the fluidic valve 288 are actively controlled by a control unit 202 of the device 200. Alternatively, the valve 288 can be embodied as a non-return valve, so that it is switched purely passively with the reversal of direction of the piston 210.

The arrangement 250 comprises in the form of the additional piston pump 212 a fluidic component downstream of the piston pump 206 with a defined fluid load characteristic. The additional piston pump 212 is arranged so as to receive temporarily a proportion of the fluid evacuated from the piston chamber 208 of the piston pump 206 during two piston chamber evacuation processes, which are described below in more detail. For this purpose the additional piston pump 212 has an additional piston chamber 214 and an additional piston 216 arranged such that it can reciprocate (see double arrow 257) in the additional piston chamber 214. The movement of the additional piston 216 is controlled by the control unit 202 of the device 200. The control unit 202 is set up for purposes of controlling the additional piston 216 such that during two piston chamber evacuation processes the additional piston 216 is moved in a controlled manner such that the fluid in from the piston chamber 208 is delivered into the additional piston chamber 214, in such a way that at the same time fluid is also supplied to the system 281. The control unit 202 is set up for purposes of controlling the additional piston 216 such that during the two piston chamber evacuation processes a flow rate of fluid downstream of the additional piston pump 212 is constant. The two piston chamber evacuation processes from the piston chamber 208 are at the same time also piston chamber transfer processes into the additional piston chamber 214, by which fluid from the piston chamber 208 is transferred, in each case into the additional piston chamber 214 (while fluid continues to be supplied to the system 281).

The arrangement 250 comprises furthermore an additional fluidic valve 218 between the piston pump 206 and the additional piston pump 212. The control unit 202, described below in more detail, is optionally set up for purposes of controlling the additional fluidic valve 218 such that during two piston chamber evacuation processes the additional fluidic valve 218 allows for a fluid flow through the additional fluidic valve 218, and between the two piston chamber evacuation processes prevents a fluid flow through the additional fluidic valve 218.

A fluid flow recording unit 277 (for example, as flow rate measuring instrument or a pressure measuring instrument) is arranged between the piston pump 206 and the additional piston pump 212, in order there to measure a flow rate or a pressure of delivered fluid. An additional fluid flow recording unit 279 (for example, a flow rate measuring instrument or a pressure measuring instrument) is arranged between the additional piston pump 212 and a fluidic system 281 connected downstream (for example, in the fluidic path shown in FIG. 1 downstream of the fluid pumping system 20, which in particular contains the sample separation unit 30), in order to measure a flow rate or a pressure of delivered fluid at the outlet of the additional piston pump 212.

The control unit 202 is set up for purposes of controlling the piston 210 and the additional piston 216 and also the additional fluidic valve 218 such that between the two piston chamber evacuation processes the additional fluidic valve 218 in a fluidic manner decouples the two piston pumps 206, 212, such that the piston chamber 208 is then filled with fluid from the supply unit 25, and the additional piston 216 is controlled so as to deliver fluid from the additional piston chamber 214 into the fluidic system 281 downstream of the additional piston pump 212.

The device 200 is designed for purposes of determining a leakage of fluid in the piston pump 206 and for this purpose comprises the control unit 202 and an determination unit 204. The control unit 202 (which can be part of the control unit 70, or can be provided separately from the control unit 70) here serves for purposes of controlling the piston 210 and the additional piston 216 such that the piston 210 executes two piston chamber evacuation processes, in each case for purposes of at least partially evacuating fluid being located in the piston chamber 208 with differing evacuation times mm the additional piston chamber 214 and into the fluidic system 281. During the two piston chamber evacuation processes the piston chamber 208 is filled with fluid, which by a movement of the piston 210 is delivered through the fluidic valve 218, which allows a fluid flow into the additional piston chamber 214. During the two piston chamber evacuation processes the additional piston 216, likewise controlled by the control unit 202, moves back along a prescribed trajectory (that is to say, in accordance with a prescribed time-space characteristic) in the additional piston chamber 214 such that the additional piston chamber 214 is partially filled with fluid. Another part of the fluid delivered from the piston chamber 208, (for example, with a constant flow rate) is delivered into the connected fluidic system 281.

The two piston chamber evacuation processes (see reference symbols II' and II" in FIG. 4 and FIG. 5), which are executed one after another, differ from one another in that these processes require a differently adjusted absolute time period, in order to transfer the piston chamber 208 from a respective initial state into a respective end state. Here, if the piston pump 206 has a leak, more fluid can escape from the arrangement 250 during the longer persisting of the two piston chamber evacuation processes than during the shorter persisting of the two piston chamber evacuation processes. This also condenses down into different flow rates, or pressure values, which are measured by means of the fluid flow recording, units 277, 279 and can be transmit-led to the determination unit 204. The determination unit 204 (which can be part of the control unit 70, or can be provided, separately from the control unit 70) can determine the leakage of the piston pump 206 based on a comparison of fluid quantities evacuated from the piston chamber 208 in the two piston chamber evacuation processes. In this determination the determination unit 204 can use the values measured by the fluid flow recording devices 277, 279 and also the trajectories of the pistons 210, 216 already known to the determination unit 204 (for example, predetermined as fixed quantities), or transmitted (for example, measured by means of encoders, not shown, on the piston pumps 206, 212).

The control unit 202 can be set up for purposes of controlling the piston 210 in such a manner that the piston executes a number of cycles of each of the two piston chamber evacuation processes with differing evacuation times, in each case for purposes of at least partially evacuating fluid located in the piston chamber 208. The determination unit 204 is set up so as to determine the leakage based on the construction of an average value from the two piston chamber evacuation processes, each of which is repeated multiple times. By means of such an averaging process measurement errors of individual measurements, or of artefacts inherent in an individual measurement, can be suppressed.

Figure 4:
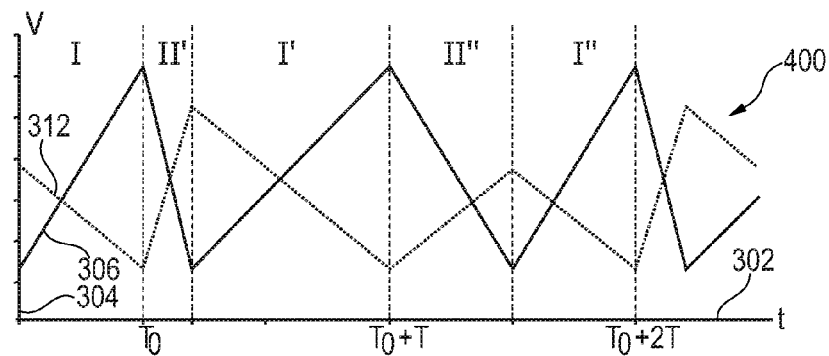
Figure 5:
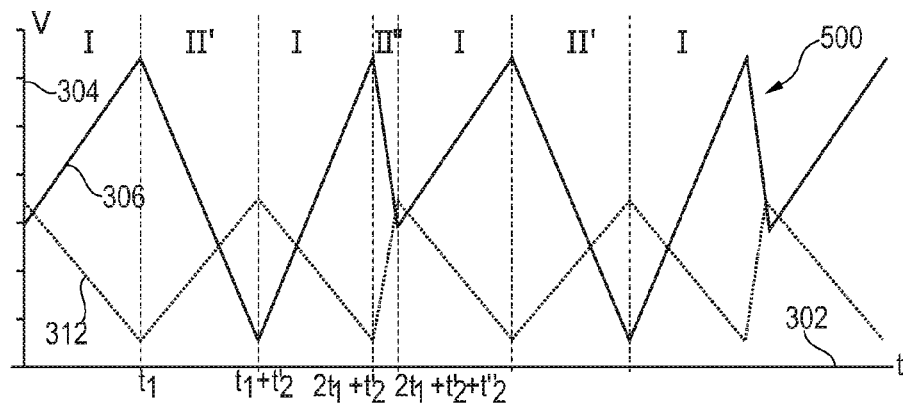

In another operating state of the arrangement 250 (which in FIG. 4 and FIG. 5 is designated as I and I' respectively, and I") between two piston chamber evacuation processes, consecutive in each case, the additional fluid valve 218 can prevent a fluidic connection between the piston pump 206 and the additional piston pump 212. In this operating state the fluidic system 281 can be fed with fluid from the additional piston chamber 214, in that the additional piston 216 then moves forwards (that is to say, upwards in FIG. 2). At the same time, by means of a reverse movement of the piston 210 (that is to say, downwards in FIG. 21, new fluid can be sucked in through the valve 288 now open, from the supply unit 25, and can be introduced into the piston chamber 208.

Thus, during one piston chamber evacuation or transfer process, the piston chamber 208, previously filled with fluid, is evacuated, in order thereby, on the one hand to fill the additional piston chamber 214 with fluid, and on the other hand to convey fluid into the fluidic system 281, if the piston chamber 208 has been evacuated to a certain degree, or completely, the fluid connection between the two piston pumps 206, 212 is interrupted by means of the fluidic valve 218. Now, during the piston chamber evacuation or transfer process, the additional fluid pump 212, filled with fluid, supplies the fluidic system 281 with fluid, while new fluid front the supply unit 25 is introduced into the fluid pump 206. A new piston chamber evacuation or transfer process can then begin.

In order to refine further the determination of the leakage of the piston pump 206 based on a number of piston chamber evacuation processes of differing durations, the determination unit 204 can also be set up so as to determine the leakage based on a comparison of a summated fluid delivery rate with an individual fluid delivery rate. The summated fluid delivery rate corresponds to a summation of fluid delivery rates of the piston 210 and the additional piston 216, if the piston 210 and the additional piston 216 are in a fluidic manner coupled with one another as a consequence of an appropriate valve setting of the additional fluidic valve 218. The individual fluid delivery rate corresponds to a fluid delivery rate of just the additional piston 216, if the piston 210 and the additional piston 216 are in a fluidic manner decoupled from one another as a consequence of another appropriate valve setting of the additional fluidic valve 218. If the fluidic valve 218 allows a fluidic coupling between the piston pump 206 and the additional piston pump 212, the fluid flowing through the fluidic system 281 is influenced by leakages of both the piston pump 206 and also the additional piston pump 212. If the fluidic valve 218 does not allow any fluidic coupling between the piston pump 206 and the additional piston pump 212, the fluid flowing through the fluidic system 281 is influenced only by leakage of the additional piston pump 212, but not by any leakage of the piston pump 206. Any difference in the fluid shortfalls between these two operating states is thus based just on leakage of the piston pump 206. This method of assessment can also be used in order to refine the accuracy of the above-described assessment method based on a number of piston chamber evacuation processes with differing evacuation time periods.

If a leakage on the piston pump 206 is identified qualitatively and/or quantitatively, the control writ 202, based on the determined leakage, can adapt or update the piston movement of the piston 210 and/or of the additional piston 216, in order to compensate wholly or partially for the fluid shortfall associated with the leakage, in particular to deliver in addition the determined fluid shortfall (for example, in order to maintain a constant flow rate).

The determination of any possible leakage of the piston pump 206 can advantageously take place during execution of a sample separation, that is to say, on-line, without the need for the sample separation process to be interrupted. In other words, the fluid delivered to the fluidic system 281 during the described leakage measurement can be introduced as a mobile phase for purposes of executing a chromatographic separation experiment, that is to say, can be supplied to the sample separation unit 30 for this purpose.

Figure 3:
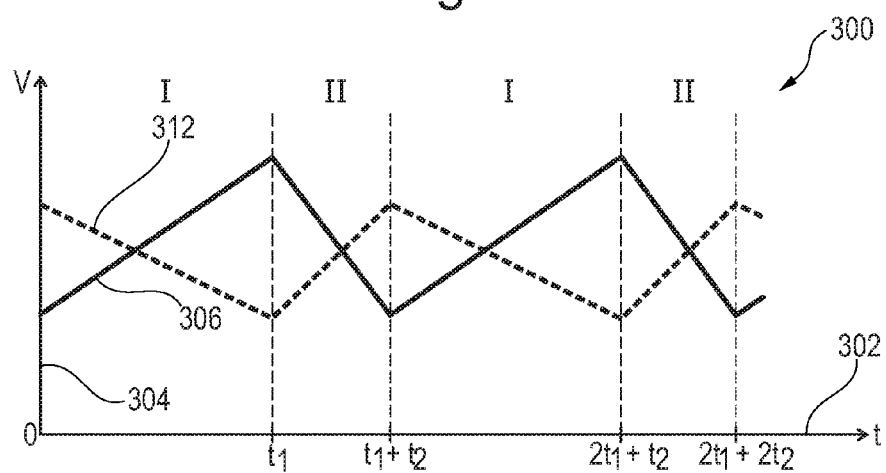
FIGS. 3 to 5 are diagrams in which there are shown piston chamber volumes bounded by pistons of two piston pumps of an arrangement for determining a leakage of fluid in one of the piston pumps, for example as a function of time, in accordance with an exemplary example of embodiment of the invention.

FIG. 3 shows a diagram 300, with time plotted along the abscissa 302, while a volume in a respective piston chamber 208, 214 is plotted along its ordinate 304; by virtue of the movement of the respective piston 210, 216 this volume varies with time. A characteristic 306 associated with the piston pump 206, and an additional characteristic 312 associated with the additional piston pump 212, are represented in FIG. 3.

In the time periods I (which in each case correspond to a time period $t_1$) the two piston pumps 206, 212 are in a fluidic manner decoupled. In this state the additional piston pump 212 supplies the fluidic system 281 with fluid, while the piston chamber 208 of the piston pump 206 is filled with fluid from the supply unit 25. In the time periods II (which in each case correspond to a time period $t_2$) the two piston pumps 206, 212 are in as fluidic manner coupled, such that the piston pump 206 supplies both the additional piston pump 212 and also the fluidic system 281 with fluid. The pumping phases associated with the characteristic curves 306, 312 in accordance with the alternating time periods I and II correspond to normal operation of the sample separation instrument 10.

FIG. 4 shows a diagram 400, in which the characteristic curves 306, 312 are adapted front those in FIG. 3 in order to execute a leakage assessment for the piston pump 206 arranged upstream.

The upper peaks of the characteristic curve 312 are lower than those of the characteristic curve 306 or, stated more precisely, fix each time period II the amplitude of the characteristic curve 306 is not less than the amplitude of the characteristic curve 312. The reason for this is that during time period II a part of the fluid volume enters into the system, and thus cannot be used for purposes of filling the additional piston chamber 214. In simple terms, the shortfall is approximately as much as the characteristic curve 312 in time period I would be reduced by, over the duration of time period II, since the slope of the characteristic curve 312 in time period I constitutes the system flow.

The time periods 11 of equal length in normal operation, as shown in FIG. 3 at now replaced by time periods II' and II" of different lengths. Here, however, the amplitude of the movement of the piston 210 (characteristic curve 306) is essentially maintained, which leads to the characteristic curves 306, 312 having ramps of differing steepness in the phases, i.e. time periods, II' and II". Incidentally, it should be noted that when the system flow is present, the amplitude of the characteristic curve 312 alters as a function of how much fluid is conveyed into the system 281 during the phase, i.e. time period, II. Accordingly, the duration of the phase, i.e. of the time period, I (I', I"), can also vary, since the slope of the characteristic curve 312 in the phase, i.e. the time period, I is prescribed by the system flow. The sum of as respective pair of time periods, that is to say, II' and I', or II" and I", is in each case essentially of equal length (in other words, summation takes place in each case over a time of duration T, assuming that no significant leakage is present and the system flow remains unaltered). In that the time periods II' and II" are selected to be of different lengths, a leakage on the piston pump 206 has a longer time to act in the longer time period II" than in the shorter time period II'. Thus, the fluid loss as a result of leakage in the piston chamber evacuation process that corresponds to the time period II' is less than that in the piston chamber evacuation process that corresponds to the time period II". Thus a discrepancy between the fluid volumes expended over equally long time sections, which in each case contain a complete phase, II' or II" respectively, is indicative of the magnitude of the leak on the piston pump 206. The discrepancy between these fluid volumes can be determined by an evaluation of the respective piston positions. An initial time point $T_0$ is also represented. A control principle in accordance with another exemplary example of embodiment is shown in a diagram 500 represented in FIG. 5. This control principle differs from that according to FIG. 4 in that the time intervals associated with the phases I are of equal length (the time period in each case is $t_1$). In other words, pairs of consecutive operating modes (I and II", or I and II") are not equidistant. The operating mode according to II' has a time period $t_2'$, and the operating mode according to II" has another (here a shorter) time period $t_2''$. Here, an advantageous aspect is that the peaks of the characteristic curve 306 are also approximately of the same height, otherwise it would be necessary when calculating a correction to take into account the difference between the fluid volumes that are being compressed.

Figure 6:
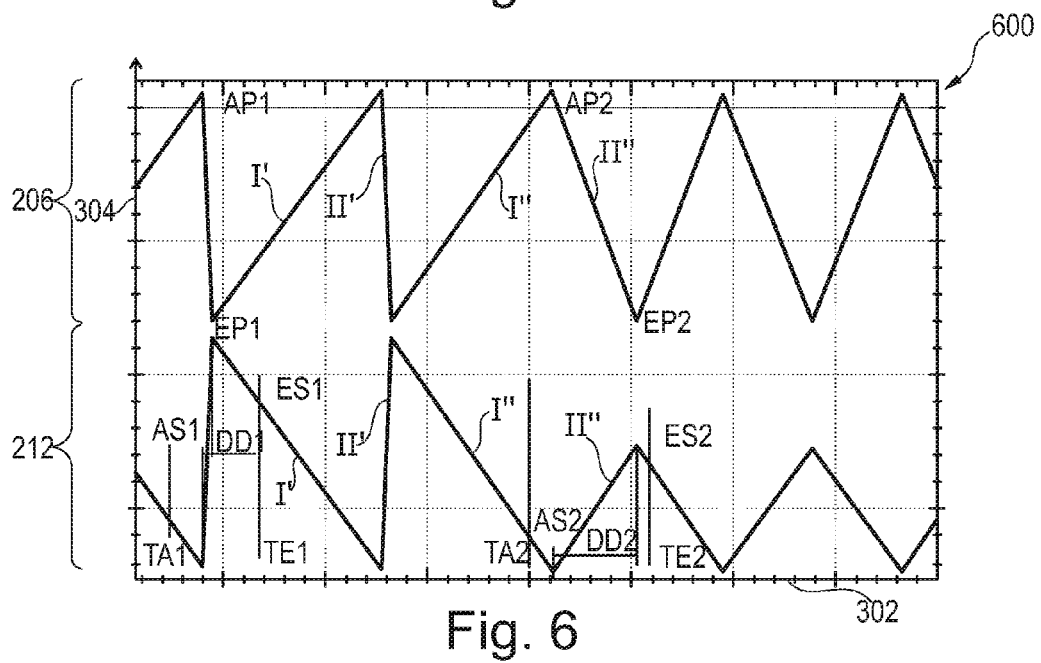
FIG. 6 shows a diagram, in which are shown piston chamber positions of pistons of piston pumps of an arrangement for determining a leakage of fluid in one of the piston pumps arranged upstream, for example as a function of time, in accordance with an exemplary example of embodiment of the invention.

FIG. 6 shows a diagram 600, in which there are shown, along the abscissa 302 the time, and along the ordinate 304 a volume (i.e. a related piston chamber position) of the pistons 210, 216 of the piston pumps 206, 212 of an arrangement for purposes of determining a leakage of fluid in a piston pump 206 arranged upstream, for example as a function of an operating time of sample separation instrument 10, in accordance with an exemplary example of embodiment of the invention.

Also, with reference to FIG. 6, in the following a further exemplary example of embodiment is described, wherein beforehand some deliberations are summarized, based on which exemplary examples of embodiment of the invention have been derived.

In accordance with an exemplary example of embodiment an HPLC pump in the form of a fluid pumping system 20 with an automated leak evaluation algorithm is created for purposes of evaluating a leak in the primary piston pump 206.

In analytical instruments such as a sample separation instrument 10 it is desirable to know as much as possible about the current state of the instrument. The statement applies also to the chromatographic pumping system 20. Modern chromatographic sample separation instruments 10, in which a piston controller is implemented in the pumping system 20, are indeed tolerant with respect to leakages in the primary piston chamber 208, which is arranged upstream of the secondary piston chamber 214. However, such leakages can serve as an early warning system for preventative maintenance, can have an influence on the accuracy of a solvent composition, and thus on the precision of a binary, or in particular a quaternary pump, and can irritate a user if they become visible as drops of liquid. Conventionally leakage detection methods have been deployed that operate externally to the actual operating method of a sample separation instrument 10, that is to say, off-line.

In accordance with an exemplary example of embodiment of the invention a leak evaluation is enabled in the primary piston chamber 208 of the piston pump 206, downstream of which is connected in a fluidic manner the secondary piston chamber 214 of the additional piston pump 212. An appropriate method can also be executed during routine operation of a pumping system 20, and even during an analytical run, that is to say, during the actual sample separation.

A principle of such a method is based on the determination of a difference in the volume of fluid lost within different measurement intervals, preferably of equal length, whereby the residence time of the pump in two different states (a) and (b), or stated more precisely, the residence time in state (b) within the measurement interval is of a different length. A first pump state (a) corresponds to at scenario in which the primary piston chamber 20 is decoupled from the fluidic system 281 by an outlet check valve in the form of the fluidic valve 218 (and is not under pressure). A second operating state (b) corresponds to a scenario in which the primary piston chamber 208 is coupled to the fluidic system (and is therefore subject to the system pressure). In the latter case (b), in contrast to the former case (a), the volume loss rate is influenced by the leakage in the primary piston chamber 208 (with the assumption that the reverse flow in the outlet check the is negligible which is usually the case).

In accordance with an exemplary example of embodiment of the invention the values that are compared with one another can be the total displaced volumes for two different strokes, which differ with regard to the time period during which the primary piston 210 is coupled to the fluidic system 281. Such differences with respect to the time period over which the piston chamber 208 is located in the state, in which it is coupled to the fluidic system 281, can be adjusted by varying the flow evacuation rate.

For the executing of such a comparison the movements of both the primary piston 210 and also the secondary piston 216 can be controlled for the two strokes such that the duration of the coupling of the primary piston chamber 208 for the two cases is different. The displaced gross volume for each one of the strokes is determined by the total alteration in position of the secondary piston 216 and the total forwards movement (and consequent displacement) of the primary piston 210. These displaced gross volumes can be compared with one another in order to take into account accompanying effects (such is for example, the compressibility of the solvent system elasticity, any thermal effects and system flow).

In order to reduce, or compensate for, the cited accompanying effects the selection of the reference points for the executed comparison can be defined in a suitable manner, in particular, the start point for the stroke of the primary piston 210 (designated as a nominal piston stroke AP1 and AP2), for the two strokes that are compared with one another, can be selected to be the same (so that the elasticity and compressibility effects are the same and therefore deliver a zero difference). Furthermore the time period between the start and the end measuring points can be selected to be identical (that is to say, TE1−TA1=TE2−TA2). This ensures the equality of the system volume losses in the two cases, makes the absolute value of the system flow irrelevant for the result of the volume loss comparison (or reduces the influence of the system flow, if the system flow was not exactly the same during the two strokes). The duration of the fastest of the piston chamber evacuation processes can preferably be adjusted to be long enough such that the thermal conditions in the residual volume remaining in the primary piston chamber 208 are not significantly different after the evacuation has been executed. The positions of the primary piston 210 are designated as EP1 and EP2. Divided by the difference between the coupled state time periods (DD2−DD1), this provides a measure for the primary leak rate. In the general case the primary leak rate LeakP, that is to say, the leak rate of the piston pump 206, can then be determined in accordance with the following formula:

$$\text{Leak}P=\{[(EP2-AP2)+(ES2-AS2)+\text{SysVol2}]-[(EP1-AP1)+(ES1-AS1)+\text{SysVol1}]\}/(DD2-DD1)$$

where:

$$SysVol = \int_{\Sigma f}^{n\varepsilon} F dt + RestThermic,$$

where the flow rate F can be determined as F~Fset~P/Paverage.

Here Fset is a predefined flow rate. P is the pressure during the respective measurement interval, and Paverage is an averaged pressure over a larger time interval under similar conditions.

The method of measurement gains in accuracy in the case in which the system pressure remains essentially constant during the measurement (for example, as a result of leakage compensation). Under these conditions the alterations in volume as a consequence of the compressibility of the fluid are not important.

RestThermic (a possible effect of a density difference as a result of the deviation in fluid temperature, for example, as a consequence of heating of the fluid during compression) can in general be calibrated for a given type of pump find a particular solvent, and in particular as a function of the type of fluid, the evacuation duration, and the length of the stroke. RestThermic can alternatively be neglected, in particular, if the shorter evacuation duration is long enough such that temperature equalization can take place in the residual volume of the cylinder 206. As the above formula for LeakP indicates, the effect of SysVol is further reduced if TE1−TA1=TE2−TA2.

A further improvement of the measurement accuracy can be achieved if the measurement duration for the two strokes is held, to be the same. It is also advantageous if the positions AS1 and AS2 are selected to be similar or equal, leading to similar or equal positions for ES1 and ES2, or vice versa (similar or equal values for ES1 and ES2 leading to similar or equal values for AS1 and AS2).

The reliability of the measurement can be further improved by averaging over a set of a plurality of pairs of strokes, which can be executed in either an interrupted or an uninterrupted series.

Position dependent leaks in the secondary piston that are located in a time of piston movement that is only active during one of the two strokes should advantageously be suppressed. A corresponding artefact can alternatively be suppressed by selecting the range of piston movement to be the same in both strokes.

Furthermore, outlet check valves, i.e. fluidic valves 218, with low leak rates can advantageously be deployed.

The influence of the thermal behavior of the solvent in the primary piston chamber 208 should be taken into account. In particular, particularly reliable results are achieved if a solvent is used with only small variations in thermal properties under thermal influences (such as for example water). Furthermore, for purposes of suppressing such effects the time periods can be selected to be long enough for the duration of the fast stroke to be sufficiently long.

A small system flow rate brings additional advantages in that the maximum stroke duration is not too severely limited. If, however, the thermal conditions are manipulated in a suitable manner (for example, are calibrated as described above) the reliability of the data can be improved by averaging, over a larger set of pairs of strokes.

Figure 7:
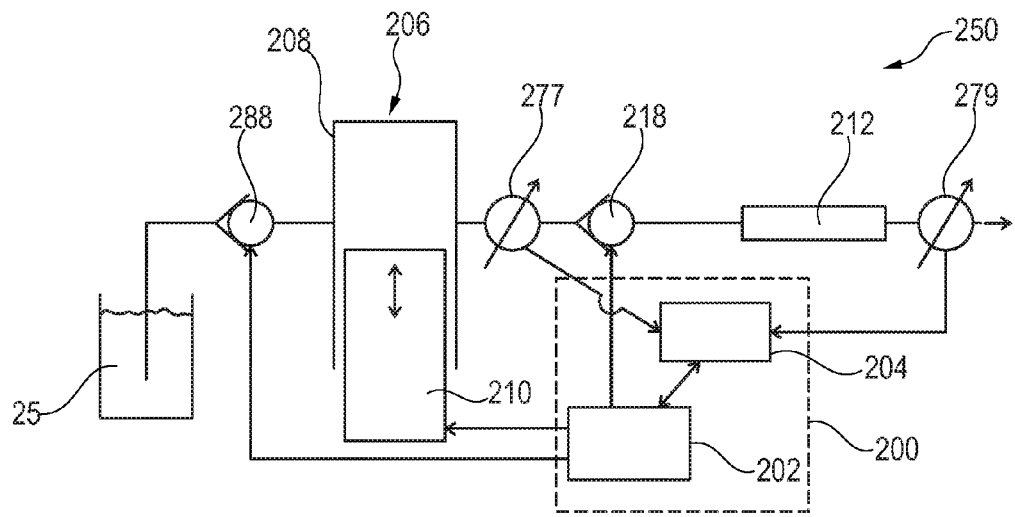
FIG. 7 shows an arrangement of a piston pump and a fluidic restrictor, and a device for determining a leakage of fluid from the piston pump, in accordance with an exemplary example of embodiment of the invention.

FIG. 7 shows an arrangement 250 of a piston pump 206 and a fluidic restrictor 212, and a device 200 for purposes of determining a leakage of fluid from the piston pump 206, in accordance with another exemplary example of embodiment of the invention.

In contrast to FIG. 2 the fluidic component downstream of the piston pump 206 is not now an additional piston pump, but rather a fluidic restrictor 212, as in FIG. 7. The latter also has a defined fluidic, or hydraulic, load characteristic and clearly serves as a type of reference for the fluidic conditions downstream of the piston pump 206.

Figure 8:
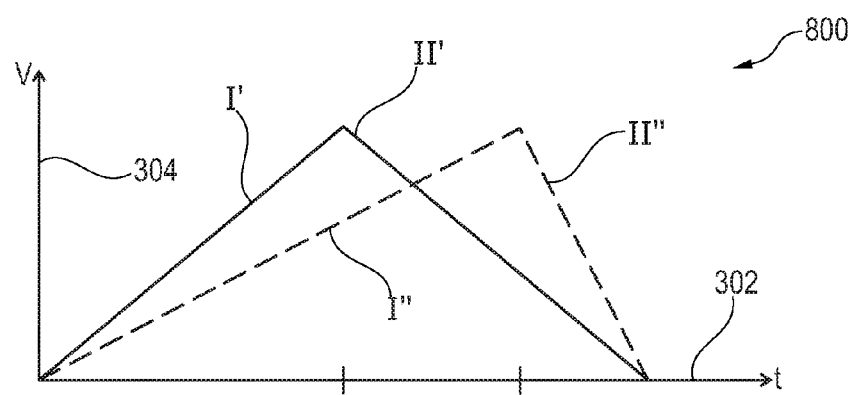
FIG. 8 shows a diagram, in which there is shown as a function of time a piston chamber volume bounded by a piston of a piston pump of an arrangement for determining a leakage of fluid in the piston pump in accordance with an exemplary example of embodiment of the invention.

FIG. 8 shows a diagram 800 that is associated with FIG. 7, in which delivery volumes of the piston pump 206 are shown for purposes of determining a leakage of fluid in the piston pump 206, in accordance with an exemplary example of embodiment of the invention. The piston 210 moves in the piston chamber 208 firstly in accordance with a position-time dependency, i.e. line, I', then in accordance with line II', subsequently along a trajectory corresponding to I" and finally along, a trajectory corresponding to II". Such a measurement arrangement should preferably contain a damping term with a time constant that is significantly longer than the duration of a stroke. A comparison of the fluid losses in the phases according to II' and II" then allows a conclusion to be drawn concerning the leakage of the piston pump 206.

It should be noted that the term "comprising" does not exclude other elements, and that the term "one" does not exclude a number of elements. Also elements that are described in conjunction with different examples of embodiment can be combined. It should also be noted that reference symbols in the claims should not be interpreted as limiting the range of protection of the claims.

The invention claimed is:

1. An arrangement, comprising
a piston pump for delivering fluid, the piston pump comprising a piston chamber and a piston arranged such that it can reciprocate in the piston chamber;
an additional piston pump in fluid connection with the piston pump, the additional piston pump comprising an additional piston chamber and an additional piston arranged such that it can reciprocate in the additional piston chamber; and
a device for determining a leakage of fluid in the piston pump, the device comprising:
a control unit for controlling the piston in such a manner that the piston executes two piston chamber evacuation processes with differing evacuation times, in each case for at least partial evacuating of fluid being located in the piston chamber; and
a determination unit for determining a leakage of fluid based on a comparison of fluid quantities evacuated from the piston chamber in the two piston chamber evacuation processes,
wherein:
the additional piston pump is arranged so as to accommodate at least temporarily a proportion of the fluid evacuated during the piston chamber evacuation processes; and
the determination unit is set up so as to determine the leakage based on a difference of a volume of fluid lost within different measurement intervals corresponding to the two piston chamber evacuation processes, wherein a residence time of the piston pump in two different pump states is of different length, and wherein the two different pump states comprise a first pump state in which the piston chamber is decoupled from the additional piston chamber and a second pump state in which the piston chamber is coupled to the additional piston chamber.

2. The arrangement in accordance with claim 1, wherein the determination unit is set up for determining the leakage when ascertaining a difference between the fluid quantity evacuated in the piston chamber evacuation process with the longer evacuation time and the fluid quantity evacuated in the piston chamber evacuation process with the shorter evacuation time.

3. The arrangement in accordance with claim 1, wherein the control unit is set up, based on the determined leakage, to adapt the piston movement so as to compensate at least partially for the fluid shortfall associated with the leakage.

4. The arrangement in accordance with claim 1, wherein the control unit is set up for controlling the piston in such a manner
that in each of the two piston chamber evacuation processes the piston is moved out of a predefined initial position of the piston in the piston chamber; and/or
that the piston in each of the two piston chamber evacuation processes is moved to a predefined end position of the piston in the piston chamber.

5. The arrangement in accordance with claim 1, wherein the determination unit is set up for determining the leakage further based on at least one of a group, which consists of a previously known movement profile of the piston, a recorded flow rate, and a recorded pressure.

6. The arrangement in accordance with claim 1, wherein the control unit is set up to specify the two piston chamber evacuation processes in such a manner that thermal conditions in the piston pump during the two piston chamber evacuation processes are matched to one another.

7. The arrangement in accordance with claim 1, wherein the control unit is set up for controlling the piston such that the piston executes each one of the two piston chamber evacuation processes a number of times, and wherein the determination unit is set up so as to determine the leakage based on an averaging over the piston chamber evacuation processes.

8. The arrangement in accordance with claim 1, furthermore comprising at least one of the following features:
the control unit is set up for controlling the additional piston in such a manner that during the two piston chamber evacuation processes the additional piston is moved in a controlled manner such that the fluid evacuated from the piston chamber is delivered into the additional piston chamber;

the control unit is set up for controlling the additional piston such that during the two piston chamber evacuation processes a pressure and/or a flow rate of fluid downstream of the additional piston pump is constant;

the two piston chamber evacuation processes are piston chamber transfer processes, in each of which fluid from the piston chamber is transferred into the additional piston chamber;

the arrangement comprises a fluidic valve between the piston pump and the additional piston pump, whereby the control unit is set up for controlling the fluidic valve in such a manner that the fluidic valve during the two piston chamber evacuation processes allows a fluid flow through the fluidic valve, and between the two piston chamber evacuation processes prevents a fluid flow through the fluidic valve, at least temporarily;

the control unit is set up for controlling the piston and the additional piston in such a manner that between the two piston chamber evacuation processes at least temporarily the piston chamber is filled with fluid and the additional piston is controlled so as to deliver fluid from the additional piston chamber into a fluidic path downstream of the additional piston pump.

9. The device in accordance with claim 1, wherein:

the control unit is configured for controlling the piston pump to deliver the fluid as a mobile phase from the piston pump into a fluidic path downstream of the piston pump, and through a separation unit positioned in the fluidic path, the separation unit configured for separating different fractions of a sample present in the mobile phase; and the device is configured for determining the leakage while the separation unit is separating the different fractions of the sample.

10. A sample separation instrument for separating a fluidic sample present in a mobile phase into fractions, wherein the sample separation instrument comprises:

the arrangement in accordance with claim 1, wherein the piston pump is configured for delivering fluid as the mobile phase, and for driving the mobile phase through the sample separation instrument; and a separation unit downstream of the piston pump for separating the different fractions of the sample present in the mobile phase.

11. The sample separation instrument in accordance with claim 10, wherein the device is configured for determining the leakage during a separation of the fluidic sample into fractions.

12. A method for determining a leakage of fluid in a piston pump, wherein the piston pump comprises a piston and a piston chamber in which the piston reciprocates, wherein an additional piston pump is arranged in fluid connection with the piston pump, the additional piston pump comprising an additional piston and an additional piston chamber in which the additional piston reciprocates, the method comprising:

controlling the piston in such a manner that the piston executes two piston chamber evacuation processes with differing evacuation times, in each case for at least partial evacuating of fluid located in the piston chamber;

determining the leakage based on a comparison of fluid quantities evacuated from the piston chamber in the two piston chamber evacuation processes, wherein:

the additional piston pump is arranged so as to accommodate at least temporarily a proportion of the fluid evacuated during the piston chamber evacuation processes; and determining the leakage is based on a difference of a volume of fluid lost within different measurement intervals corresponding to the two piston chamber evacuation processes, wherein a residence time of the piston pump in two different pump states is of different length, and wherein the two different pump states comprise a first pump state in which the piston chamber is decoupled from the additional piston chamber and a second pump state in which the piston chamber is coupled to the additional piston chamber.

13. The method in accordance with claim 12, wherein in the method the determining of the leakage is executed during a separating of a fluidic sample being present in a mobile phase into fractions, wherein the fluid is delivered as the mobile phase by the piston pump.

\* \* \* \* \*